United States Patent [19]

Olesen et al.

[11] Patent Number: Plant 6,939

[45] Date of Patent: Jul. 25, 1989

[54] ROSE PLANT NAMED POULONI

[75] Inventors: Pernille Olesen; Mogens N. Olesen, both of Fredensborg, Denmark

[73] Assignee: Weeks Wholesale Rose Growers, Inc., Ontario, Calif.

[21] Appl. No.: 168,432

[22] Filed: Mar. 15, 1988

[51] Int. Cl.[4] ..... A01H 5/00

[52] U.S. Cl. ..... Plt./11

[58] Field of Search ..... Plt. 11

[56] References Cited

PUBLICATIONS

Meikle, C. E. (Ed.) (1980), *Modern Roses,* 8, The McFarland Company, Harrisburg, Pa., p. 534.

*Primary Examiner*—James R. Feyrer

*Attorney, Agent, or Firm*—Vincent G. Gioia

[57] ABSTRACT

A new hybrid tea rose variety of Jasper Red and Orient Pink coloring.

1 Drawing Sheet

The present invention relates to a new and distinct variety of rose plant of the hybrid tea rose class, which was originated by my crossing as seed parent the rose known as "Kalahari" and the rose known as "Nitouche" as pollen parent. The new rose is known by the denomination "Pouloni".

Among the novel characteristics possessed by this new variety which distinguish it from its parents and all other varieties of which I am aware are flowers of unusual Jasper Red with darker toned petal undersurfaces and lighter petal top surfaces. Asexual reproduction by budding of the new variety as performed in Fredensborg, Denmark, shows that the foregoing and other distinguishing characteristics come true to form and are established and transmitted through succeeding propagations.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with The Royal Horticultural Society Colour Chart (R.H.S.C.C.). The terminology used in color description herein refers to plate numbers in the aforementioned color chart, e.g., "46B" is plate 46B of The Royal Horticultural Society Colour Chart.

Parentage: Seedling.

*Seed parent.*—"Kalahari".

*Pollen parent.*—"Nitouche".

Class: Hybrid Tea.

The following observations are made of specimens grown under glass in Fredensborg, Denmark during the month of October.

FLOWER

Blooming habit: Continuous.

A. Bud:

(1) *Size.*—Medium.

(2) *Form.*—Ovoid.

(3) *Color.*—After sepals fall, near 46B.

(4) *Sepals.*—Normal, similar length to bud.

(5) *Peduncle.*—Length — long. Aspect — straight. Strength — erect. Color — purplish red.

B. Bloom:

(1) *Size.*—Average size when fully expanded — about 3½ to 4 inches.

(2) *Borne.*—Singly and small sprays.

(3) *Form.*—Decorative, petals roll under and are ruffled.

(4) *Petalage.*—Number of petals under normal conditions — about 22.

(5) *Color.*—As sepals fall and petals begin to unfurl, bud coloring becomes near 39A, Jasper Red. Some dark splotching may be seen on immature outer bud petals and petal veining and some washing with lighter toned hightlights are also evident. However, washing of mixed tones is more visible on petal top surfaces, especially on outer petals where tonality differences are somewhat greater. Petal undersurfaces continus near Jasper Red, 39A, but tend to lighten on inner petals, approaching near 39D in mature blooms. Petal top surfaces are substantially lighter than undersurfaces, becoming near 27D as flowers age. Outer petals have a range of lighter toned washing on petal top surfaces from near Orient Pink 36D to near Azalea Pink 39D to Jasper Red at petal edges.

C. Petals:

(1) *Texture.*—Thick.

(2) *Appearance.*—Inside — velvety and outside — satiny.

(3) *Form.*—Broad fan shaped, ruffled.

(4) *Arrangement.*—Regularly arranged — shingle-like.

(5) *Petaloids in center.*—Few.

(6) *Persistence.*—Drop off cleanly.

(7) *Fragrance.*—Slight.

(8) *Lasting quality.*—Very long lasting on plant and as cut flower.

REPRODUCTIVE ORGANS

A. Stamens, filaments and anthers:

*Arrangement.*—Stamens regularly arranged around styles, joined at base, filaments orange with some red, anthers yellow.

B. Pollen:

*Color.*—Yellow.

C. Styles: Bunched, even, medium length.

D. Stigmas:

Color.—Orange with some red.

E. Hips: Ovoid, large, orange-yellow when mature.

PLANT

A. Form: Bushy, spreading.

B. Growth: Very vigorous, uniform branching attaining height of about 4 feet.

C. Foliage: Compound 5 leaflets.

(1) *Size.*—Medium.

(2) *Quantity.*—Abundant.

(3) *Color.*—New foliage: purplish red. Old foliage: Upper side — dark green, glossy. Under side — dull.

(4) *Shape.*—Oval, pointed.

(5) *Texture.*—Upper side shiny, leathery and under side is dull, leathery.

(6) *Edge.*—Serrated.

(7) *Serration.*—Regular.

(8) *Leaf stem.*—Color — dark green with red stripes. Under side — dark green, dull.

(9) *Stipules.*—Medium, pointed.

(10) *Resistance to disease.*—Blackspot — good. Mildew — excellent. Rust — very good.

D. Wood:

(1) *New wood.*—Color — dark purplish to green. Bark — smooth.

(2) *Old wood.*—Color — dark green to purplish. Bark — smooth.

E. Thorns.—Quantity (main stalk) — ordinary. On laterals from stalk — few. Form — long pointed. Length — medium. Color — deep purple. Position — ordinary.

(2) *Prickles.*—Very few.

F. Winter hardiness: Very hardy in winter.

We claim:

1. A new and distinct variety of rose plant of the hybrid tea rose class, substantially as shown and described, characterized particularly by decorative, Jasper Red and Orient Pink flowers borne singly and in small sprays on a disease resistant plant.

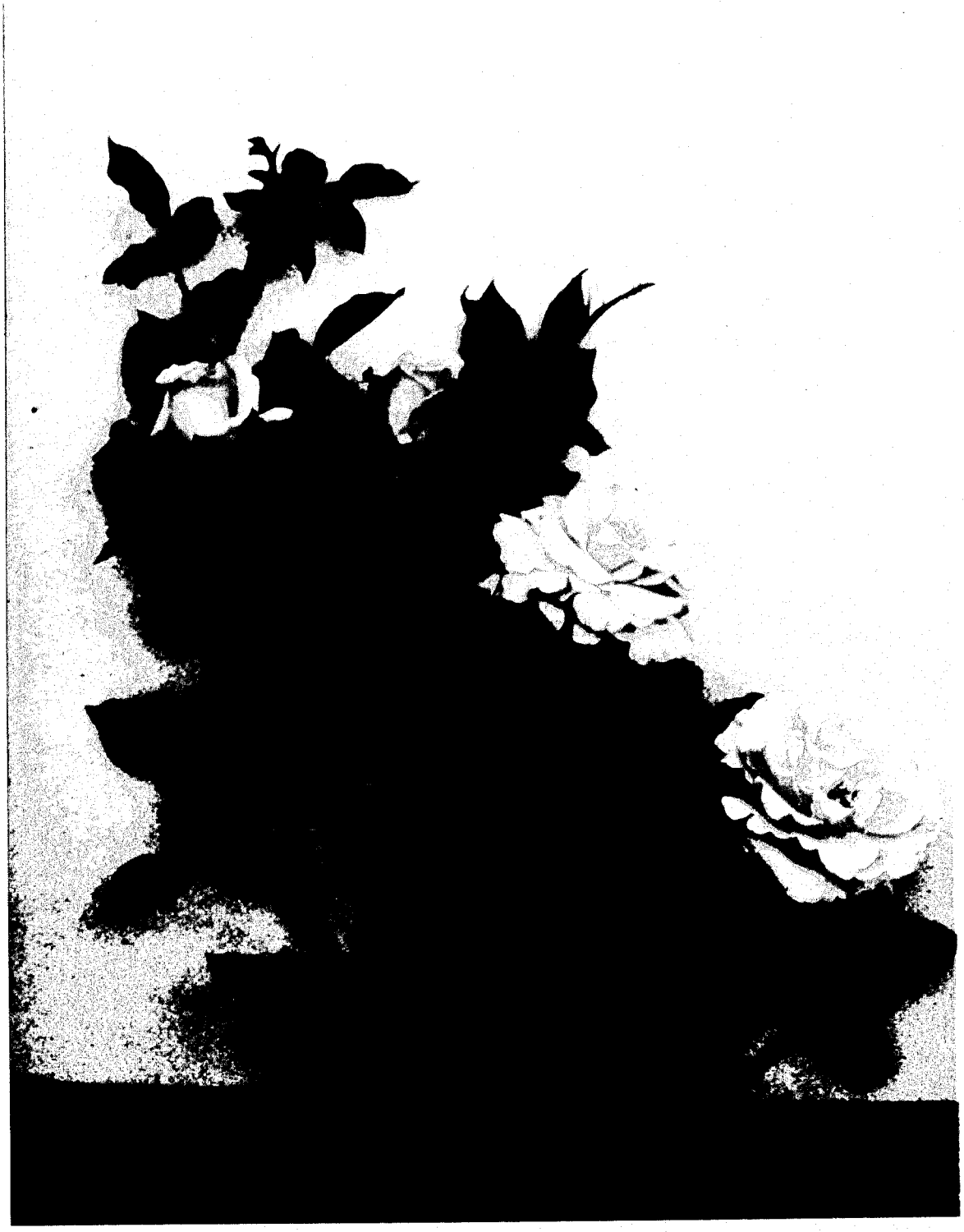

* * * * *